United States Patent
Agarkhed et al.

(10) Patent No.: US 10,869,862 B2
(45) Date of Patent: Dec. 22, 2020

(54) ANTIMICROBIAL COMPOSITIONS FOR TOPICAL USE

(71) Applicant: Conopco, Inc., Englewood Cliffs, NJ (US)

(72) Inventors: Ajit Manohar Agarkhed, Thane (IN); Mohini Anand Bapat, Mumbai (IN); Amitabha Majumdar, Bangalore (IN); Mruthyunjaya Swamy Mathapathi, Bangalore (IN); Nikita Tomar, Nagpur (IN)

(73) Assignee: CONOPCO, INC., Englewood Cliffs, NJ (US)

( * ) Notice: Subject to any disclaimer, the term of this patent is extended or adjusted under 35 U.S.C. 154(b) by 0 days.

(21) Appl. No.: 16/303,299

(22) PCT Filed: May 4, 2017

(86) PCT No.: PCT/EP2017/060627
§ 371 (c)(1),
(2) Date: Nov. 20, 2018

(87) PCT Pub. No.: WO2017/202586
PCT Pub. Date: Nov. 30, 2017

(65) Prior Publication Data
US 2019/0209544 A1    Jul. 11, 2019

(30) Foreign Application Priority Data
May 26, 2016 (EP) .................................. 16171501

(51) Int. Cl.
*A61K 31/455* (2006.01)
*A61K 9/00* (2006.01)
*A61K 47/10* (2017.01)
*A61P 31/04* (2006.01)

(52) U.S. Cl.
CPC .......... *A61K 31/455* (2013.01); *A61K 9/0014* (2013.01); *A61K 47/10* (2013.01); *A61P 31/04* (2018.01)

(58) Field of Classification Search
CPC .... A61K 31/455; A61K 47/10; A61K 9/0014; A61P 31/04
See application file for complete search history.

(56) References Cited

U.S. PATENT DOCUMENTS

| | | | |
|---|---|---|---|
| 3,592,933 A | 7/1971 | Kullenberg | |
| 5,167,950 A | 12/1992 | Lins | |
| 5,968,528 A | 10/1999 | Deckner et al. | |
| 6,551,604 B1 | 4/2003 | Beck | |
| 2003/0211058 A1 | 11/2003 | Matts et al. | |
| 2003/0211068 A1 | 11/2003 | O'Prey et al. | |
| 2009/0220445 A1 | 9/2009 | Iwata et al. | |
| 2011/0287074 A1* | 11/2011 | Jin | A01N 55/00 424/401 |
| 2014/0364509 A1 | 12/2014 | Wegner | |
| 2015/0258003 A1 | 9/2015 | Copeland et al. | |

FOREIGN PATENT DOCUMENTS

| | | |
|---|---|---|
| CN | 104382766 | 3/2015 |
| DE | 102013009341 | 12/2014 |
| JP | 2003300810 | 10/2003 |
| WO | WO0222102 | 3/2002 |
| WO | WO06111256 | 10/2006 |
| WO | WO2012152567 | 11/2012 |
| WO | WO2015172801 | 11/2015 |
| WO | WO2017202586 | 11/2017 |

OTHER PUBLICATIONS

Search Report and Written Opinion in PCTEP2017060627; dated Jul. 11, 2017.
Search Report and Written Opinion in EP16171501; dated Nov. 15, 2016.
Written Opinion 2 in PCTEP2017060627; dated Apr. 24, 2018.
Search Report and Written Opinion in EP18161444; dated Jun. 9, 2018; European Patent Office (EPO).
Search Report and Written Opinion in PCTEP2019054028; dated Apr. 25, 2019; World Intellectual Property Org. (WIPO).
Co-pending Application, Bapat et al., filed Aug. 27, 2020, U.S. Appl. No. 16/976,139.

* cited by examiner

*Primary Examiner* — Savitha M Rao
(74) *Attorney, Agent, or Firm* — Krista A. Kostiew

(57) ABSTRACT

This invention relates to an antimicrobial composition for application onto human skin, said composition comprising: a. 20 to 90 wt. % of one or more $C_2$ to $C_4$ monohydric alcohols; b. 0.5 to 10 wt. % vitamin B3 compound; c. 1 to 20 wt. % of one or more polyols; and wherein the weight ratio of the vitamin B3 compound to the one or more polyols is in the range of 1:2 to 1:20 and wherein the viscosity of the composition is in the range of 0.5 Pa s (500 cps) to 18 Pa s (18000 cps) at 25° C. wherein the one or more $C_2$ to $C_4$ monohydric alcohols are selected from ethanol, isopropyl alcohol and combinations thereof and further wherein the composition comprises a combination of ethanol and isopropyl alcohol.

10 Claims, No Drawings

ANTIMICROBIAL COMPOSITIONS FOR TOPICAL USE

FIELD OF THE INVENTION

The invention relates to antimicrobial compositions for topical use, i.e. for application onto the human skin. The antimicrobial compositions of the present invention comprise a vitamin B3 compound and provide long term protection against pathogens and other unwanted micro-organisms.

BACKGROUND OF THE INVENTION

Antiseptics are antimicrobial substances that are applied to living tissues, e.g. skin, to reduce the possibility of infection. Antiseptics are generally distinguished from antibiotics by the latter's ability to be transported through the lymphatic system to destroy bacteria within the body, and from disinfectants, which destroy microorganisms found on non-living objects.

Skin generally contains several different microorganisms in concentrations exceeding millions or even billions of colony forming units (cfu) per square centimetre ($cm^2$). Many of these microorganisms are harmless, but there are also various pathogenic species present, such as *E. coli* or *S. aureus*. Also other unwanted bacteria are found on the skin, such as *S. epidermidis*, which is generally non-pathogenic, but is thought to be causing an unpleasant body odour.

Skin hygiene is of high priority to present day consumers. Liquid antimicrobial compositions are generally used by consumers for immediate protection against microorganisms. An example is the use of hand sanitizers suitable for sanitising hands without using water.

A common ingredient in liquid antimicrobial compositions are alcohols, usually ethanol or isopropanol. Alcohols, however, have short term activity due to their rapid evaporation. Alcohols are most effective when combined with distilled water. A mixture containing 60% total alcohols is effective against wide spectrum of bacteria.

US 2015/258003 A1 (Gojo Industries Inc) describes an effective healthcare personnel hand wash composition that maintains or improves skin hydration, the composition comprises at least one $C_1$-$C_6$ alcohol, at least one phytochemical with anti-inflammatory properties, at least one enzyme or coenzyme that aids in the formation of the stratum corneum and a deposition enhancer. Vitamin B3 (niacin) is mentioned as an example of a stratum corneum formation enhancer.

CN104382766 A (Ou Lingong, 2015) discloses an example of an anti marks composition that contains 0.8%, polyvinypyrrolidone, 1.5%, *Hydrocotyle asiatica* extract 0.7%, Astragaloside A 0.5%, the aloe extract 8%, *coix* seed extract 9%, purslane extract 4.5%, Vitamin B3 3.5%, ethanol 35%, propylene glycol 9% and water 27.5%.

Vitamin B3 or the amide thereof (niacinamide) are both mentioned in the prior art as a suitable ingredient for skin care products, because vitamin B3 and niacinamide are known to comprise several properties that are advantageous for the skin, such as the prevention of cellulite, enhancement of stratum corneum formation, treatment of skin irritation and improvement of absorption of water into the skin. Niacinamide is also used as a skin lightening active. In addition, niacinamide is used in the treatment of many inflammatory skin conditions like Acne vulgaris, Psoriasis and Atopic dermatitis.

WO 2002/22102 A1 (Johan Asplund) describes a cosmetic composition suitable for topical application to the skin or hair comprising:
  (a) from about 0.0001% to about 10%, by weight, of biologically active enzyme;
  (b) from about 0.1% to about 20%, by weight, of polyhydric alcohol; and
  (c) from about 0.1% to about 20%, by weight, of skin care active selected from a vitamin B3 component, panthenol, vitamin E, vitamin E acetate, retinol, retinyl propionate, retinyl palmitate, retinoic acid, vitamin C, theobromine, alpha-hydroxyacid, farnesol, phytantriol, salicylic acid, and mixtures thereof.

WO 2015/172801 A1 (Unilever) describes the use of niacinamide for inducing the secretion of anti-microbial peptides (AMPs) by keratinocytes when applied on an external surface of the human body. In the examples of this document the niacinamide is added to Vaseline™ and applied to the skin.

One of the problems associated with the application of vitamin B3 or niacinamide in aqueous compositions is the formation of deposits.

SUMMARY OF THE INVENTION

The inventors of the present invention have surprisingly found that a composition comprising a combination of 20 to 90 wt. % $C_2$-$C_6$ monohydric alcohols and 0.5-10 wt. % of a vitamin B3 compound provides synergistic protection against microorganisms when applied on the human skin.

In comparison to the usage of solely $C_2$-$C_6$ monohydric alcohols or solely vitamin B3 compound, the combined application of these antimicrobial components in accordance with the present invention provides prolonged protection against bacteria.

The inventors have further found that the presence of 1 to 20 wt. % of one or more polyols in the antimicrobial composition prevents the formation of deposits, especially if the vitamin B3 compound and the one or more polyols are present in a weight ratio of at least 1:20.

Therefore the present invention relates to an antimicrobial composition for application onto human skin, said composition comprising:
  a. 20 to 90 wt. % of one or more C2 to C4 monohydric alcohols;
  b. 0.5 to 10 wt. % vitamin B3 compound;
  c. 1 to 20 wt. % of one or more polyols; and
wherein the weight ratio of the vitamin B3 compound to the one or more polyols is in the range of 1:2 to 1:20 and wherein the viscosity of the composition is in the range of 0.5 Pa s (500 cps) to 18 Pa s (18000 cps) at 25° C. wherein said monohydric alcohols are selected from ethanol, isopropyl alcohol and combinations thereof and further wherein the composition comprises a combination of ethanol and isopropyl alcohol.

The inventors have found that antimicrobial compositions meeting the aforementioned viscosity requirement are easy to apply and spread out across the skin, e.g. by rubbing.

The features and advantages of the invention will become apparent to those of ordinary skill in the art from a reading of the following detailed description and the appended claims. For the avoidance of doubt, any feature of one aspect of the present invention may be utilized in any other aspect of the invention. The word "comprising" is intended to mean "including" but not necessarily "consisting of" or "composed of." In other words, the listed steps or options need not be exhaustive. It is noted that the examples, embodiment and figures given in the description below are intended to clarify the invention and are not intended to limit the invention to those examples per se.

Unless otherwise specified, numerical ranges expressed in the format "from x to y" are understood to include x and y. In specifying any range of values or amounts, any particular upper value or amount can be associated with any particular lower value or amount. Except in the examples and comparative experiments, or where otherwise explicitly indicated, all numbers are to be understood as modified by the word "about". All percentages and ratios contained herein are calculated by weight unless otherwise indicated. As used herein, the indefinite article "a" or "an" and its corresponding definite article "the" means at least one, or one or more, unless specified otherwise. The various features of the present invention referred to in individual sections above apply, as appropriate, to other sections mutatis mutandis. Consequently features specified in one section may be combined with features specified in other sections as appropriate. Any section headings are added for convenience only, and are not intended to limit the disclosure in any way. The invention is not limited to the embodiments illustrated in the drawings. Accordingly it should be understood that where features mentioned in the claims are followed by reference numerals, such numerals are included solely for the purpose of enhancing the intelligibility of the claims and are in no way limiting to the scope of the claims. The examples are intended to illustrate the invention and are not intended to limit the invention to those examples per se.

DETAILED DESCRIPTION OF THE INVENTION

A first aspect of the invention relates to an antimicrobial composition for application onto human skin, said composition comprising:
  a. 20 to 90 wt. % of one or more $C_2$ to $C_4$ monohydric alcohols;
  b. 0.5 to 10 wt. % vitamin B3 compound;
  c. 1 to 20 wt. % of one or more polyols; and
wherein the weight ratio of the vitamin B3 compound to the one or more polyols is in the range of 1:2 to 1:20 and wherein the viscosity of the composition is in the range of 0.5 Pa s (500 cps) to 18 Pa s (18000 cps) at 25° C. wherein said monohydric alcohols are selected from ethanol, isopropyl alcohol and combinations thereof and further wherein the composition comprises a combination of ethanol and isopropyl alcohol.

The term "antimicrobial composition" as used herein refers to a composition that is capable of killing bacteria or of inhibiting their growth.

The term "monohydric alcohols" as used herein refers to alcohols containing one hydroxyl group.

The term "vitamin B3 compound" as used herein refers to vitamin B3, i.e. niacin, the amide of vitamin B3, i.e. niacinamide or nicotinic amide, niacinamide analogues and combinations thereof.

The term "polyols" as used herein refer to alcohols containing multiple hydroxyl groups.

The term "viscosity" as used herein refers to the viscosity measured at 25° C. by a Brookfield RV Viscometer, using spindle 4, 10 rpm for 30 sec in a beaker wherein the spindle probe is immersed in the antimicrobial composition to the mark indicated on the spindle probe. Several units are known to be used in the context of viscosity but the one used more often are cps, Pa s and mPa s and these units are easily inter-convertible with the help of publically available resources like text books, encyclopedias and the internet.

The term "monophasic" as used in this description refers to compositions comprising solely one phase, e.g. an aqueous phase. An emulsion for example comprises two phases.

The antimicrobial composition according to the invention is preferably a leave-on composition. The composition is preferably transparent.

The antimicrobial composition according to the invention is preferably a liquid at 20° C. The antimicrobial composition according to the invention is preferably monophasic.

The antimicrobial composition preferably is a liquid or thixotropic gel.

The weight ratio of the vitamin B3 compound to the one or more polyols in the composition according to the invention is preferably in the range of 1:3 to 1:15, even more preferably in the range of 1:4 to 1:10.

The viscosity of the composition according to the invention is preferably in the range of 1 Pa s (1000 cps) to 15 Pa s (15000 cps) at 25° C. More preferably the range of viscosity is of 4 Pa s (4000 cps) to 12 Pa s (12000 cps) at 25° C.

The composition preferably comprises 30 to 80 wt. % of the combination of $C_2$ to $C_4$ monohydric alcohols wherein said monohydric alcohols are selected from ethanol, isopropyl alcohol and combinations thereof and further wherein the composition comprises a combination of ethanol and isopropyl alcohol, more preferably 40 to 75 wt. % of the $C_2$ to $C_4$ monohydric alcohols, most preferably the composition comprises 55 to 70 wt. % of the $C_2$ to $C_4$ monohydric alcohols.

Preferably, the antimicrobial composition contains 30 to 80 wt. %, more preferably 40 to 70 wt. % and most preferably 50 to 68 wt. % ethanol.

The antimicrobial composition preferably comprises 0.5 to 8 wt. % of the vitamin B3 compound. More preferably the composition comprises 0.6 to 5 wt. % of the vitamin B3 compound, even more preferably at least 0.75 wt. % and most preferably at least 1 wt. % of the vitamin B3 compound.

In a preferred embodiment the vitamin B3 compound is selected from niacin, niacinamide and combinations thereof. In a more preferred embodiment the vitamin B3 compound is niacinamide.

In a preferred embodiment the composition according to the invention comprises 2 to 15 wt. % of the one or more polyols. In a more preferred embodiment the composition comprises 3 to 10 wt. % of the one or more polyols.

Preferred polyols in the composition according to the invention are selected from sorbitol, glycerol, polyethylene glycol, propylene glycol and combinations thereof. Even more preferred polyols in the composition are glycerol, polyethylene glycol, propylene glycol and combinations thereof. Most preferred are propylene glycol, polyethylene glycol and combinations thereof. Even most preferred is propylene glycol.

In a preferred embodiment the polyethylene glycols have an average molecular weight below 1000 Da. More preferred are polyethylene glycols with an average molecular weight from 100 to 800 Da, most preferred are polyethylene glycols with an average molecular weight from 200 to 600 Da.

The antimicrobial composition preferably comprises 10 to 40 wt. % of water. More preferably the composition comprises 12 to 35 wt. % of water, most preferably 25 to 30 wt. % of water.

The composition preferably comprises 0.01 to 1 wt. % of a thickening agent. More preferably the composition comprises 0.05 to 0.8 wt. % of a thickening agent, most preferably 0.08 to 0.2 wt. % of a thickening agent.

The thickening agent in the composition according to the invention is preferably selected from homopolymers, copolymers and combinations thereof, wherein said homopolymers and copolymers comprise monomers selected from acrylic acid, acrylates, compounds comprising an acrylate group and combinations thereof.

The composition preferably comprises a basic neutralizer, which is preferably selected from triethanaolamine, tromethamine, aminomethylpropanol, tetrahydroxypropyl ethylenediamine, triisopropanolamine and combinations thereof. The most preferred basic neutralizer is aminomethylpropanol, e.g. AMP-95.

In a preferred embodiment the composition according to the invention comprises 0 to 15 wt. % of optional ingredients such as chelating agents, colorants, perfumes, skin conditioning agents, vitamins other than vitamin B3, and combinations thereof.

The composition preferably comprises skin conditioning agents and these skin conditioning agents are preferably selected from silicones, siloxanes and combinations thereof.

The composition preferably comprises vitamins other than vitamin B3 and these vitamins are preferably selected from vitamin A, vitamin E and combinations thereof. Even more preferably the composition contains vitamin E.

A second aspect of the invention relates to the use of the antimicrobial composition, as is described herein before as an antiseptic said use comprising applying the antimicrobial composition onto the human skin.

The invention will now be further described with reference to the non-limiting examples.

EXAMPLES

Example 1

Preparation of Antimicrobial Compositions

Three antimicrobial compositions were prepared on the basis of the recipes shown in Table 1.

TABLE 1

| Ingredients | Product 1 (wt. %) | Product A (wt. %) | Product B (wt. %) |
|---|---|---|---|
| Ethanol | 62 | — | 55 |
| Isopropyl alcohol | 3 | — | 10 |
| Nicacinamide | 1 | 1 | — |
| Glycerine | — | — | 1 |
| Propylene glycol | 5 | — | — |
| Carbomer ® 980 | 0.325 | — | 0.350 |
| AMP-95 ® | 0.1 | — | 0.147 |
| Water | Up to 100% | Up to 100% | Up to 100% |

Product B corresponds to an antimicrobial composition currently available on the market.

Product 1 was prepared as follows: First the thickening agent, Carbopol® 980, was slowly added to the water until a clear mixture was obtained. While the mixture was being continuously mixed at 250 rpm, the following ingredients were added to the mixture in consecutive order: monohydric alcohols and 6% aqueous solution of the basic neutralizer AMP-95® (aminomethyl propanol). After the addition of the basic neutralizer the pH and viscosity was measured and the pH was adjusted to a pH in the range of 6.5 to 7.5 by adding, if needed, additional 6% aqueous solution of the basic neutralizer AMP-95®. Subsequently a clear pre-mixed aqueous solution of niacinamide and propylene glycol was added to the mixture while being continuously mixed.

Product A was prepared by adding 1 wt. % of niacinamide to 99 wt. % of distilled water to obtain a 1 wt. % niacinamide solution. Product B was prepared in a similar way as product 1.

Protocol for Testing the Antimicrobial Efficiency of the Antimicrobial Compositions The protocol had multiple steps which are described hereinafter.

Prewash (7 Days):

Each test subject received a non-antimicrobial soap and received instructions for 7 days to use only this soap for bathing and washing hands and was instructed to refrain from using leave-on products, such as sun screen or body lotion.

On day 8, three times an area of 12.25 $cm^2$ area (3.5×3.5 cm) was marked on one of the inner forearms using a marker pen and scale. Then a circular area of 7.07 $cm^2$±0.2 was marked with a surgical marker pen inside each box on the assigned forearm, using a template. One additional circular area of 7.07 $cm^2$±0.2 was marked outside the boxes on the forearm where no products would be applied (untreated control). At least 2 cm±0.2 cm of space was left between the boxes.

After the marking of all the test areas, each test subject was instructed to wash their forearm according to the following instructions.

a. Wet/dip the non-antimicrobial soap for 10 seconds in sterile distilled water with a temperature of 24° C.±2° C.
b. Wet each forearm with sterile water (100 ml±10 ml).
c. Rub the soap 5 times back and forth across the length of the forearm.
d. Add 5 ml±1 ml of sterile water on forearm and lathered for 15 seconds.
e. Wash forearm with sterile water to remove the soap completely.
f. Remove excess water by patting dry by using sterile tissue paper 92 mg of each tested antimicrobial composition was spread inside the designated test areas and the composition was spread inside the delineated areas on the forearm. This spreading was done using gloves. The formulation is spread over the area for 1 to 2 min. There was no product application on the untreated site. Product A was applied drop by drop and then spread by pipette tip.

After application of all antimicrobial compositions, the test subjects were instructed to wait for 6 hours±15 minutes in a controlled environment room at 24±2° C. and 45%±10% relative humidity with their forearms not touching any other surface or wetting their forearms.

*E. coli* Culture Application and Cup-Scrub Sampling Procedure 15 to 30 minutes before the expiry of the waiting period, the *E. coli* ATCC 10536 sample ($1.0 \times 10^8$ to $5.0 \times 10^8$ cells/ml) was prepared in 10 mM sterile sodium phosphate buffer. Application of *E. coli* culture was done under controlled conditions of 24±2° C. and 45%+10% relative humidity.

After 6 hours±15 minutes' post product application, 10 µl (±0.1 µl), post vortexing, of *E. coli* ATCC 10536 sample was added and spread uniformly using the pipette tip, inside the test areas leaving 0.2 cm from the marking, and the timer was started. During the application and recovery of the *E. coli* culture, subjects were asked to keep their forearms and hands resting on the table with palms facing up.

After 5 minutes±10 s of contact time of E. coli on the forearm, the sterile sampling cylinder (diameter 3 cm) was placed on the area where E. coli was applied. 1.5 ml of sterile sampling solution was pipetted into the cylinder. The cup was held firmly against the skin surface to ensure that the sampling fluid does not leak from the sampling site.

The entire area of skin inside the cup was scrubbed in all directions with moderate pressure for 60 s±5 s using a sterile blunt ended rod. After scrubbing, the entire sampled fluid was transferred by pipetting into a sterile labelled microfuge or similar tube. The same process was repeated once again for another 60 seconds±5 seconds and both samples were pooled together. After the sample was collected, the site was blotted dry with clean tissue papers.

The above E. coli application and sampling procedure was performed for all the test areas. Simultaneously, samples were processed for counting the number of alive E. coli bacteria that survived the exposure to the tested areas, using standard microbiological methods.

On completion of testing, subjects were informed to perform a 1-minute rinse/rub with Becton Dickinson (BD) 70% isopropyl alcohol swabs on the fore-arm and to air-dry, followed by a supervised 4-minute wash with a 4% chlorhexidine gluconate solution. Then subjects were asked to wash their forearms and palms with soap.

Results

The number of bacteria that survived the exposure to the test areas are expressed as the residual log survival. Thus, a residual log survival of 3, corresponds to $10^3$ of surviving E. coli bacteria. The results are displayed in table 2 below.

TABLE 2

|  | Residual log survival |
|---|---|
| Product 1 | 2.22 |
| Product A | 3.26 |
| Product B | 5.43 |

The viscosity of product 1 at 25° C. was approximately 6 Pa s (6000 cps). This was measured using a Brookfield RV Viscometer, using spindle 4 at 10 rpm for 30 seconds in a beaker wherein the spindle probe is immersed in the product to the mark indicated on the spindle probe.

Example 2

A similar experiment as described in Example 1 was performed with antimicrobial compositions that had been prepared on the basis of the recipes shown in Table 3.

TABLE 3

| Ingredients | Product 2 (wt. %) | Product C (wt. %) |
|---|---|---|
| Ethanol | 62 | 62 |
| Isopropyl alcohol | 3 | 3 |
| Niacinamide | 1 | — |
| Propylene glycol | 5 | 5 |
| Carbomer ® 980 | 0.325 | 0.325 |
| AMP-95 ® | 0.1 | 0.1 |
| Water | Up to 100% | Up to 100% |

Results

The results are displayed in the table below.

TABLE 4

|  | Residual log survival |
|---|---|
| Product 2 | 2.88 |
| Product C | 3.43 |

Example 3

A similar experiment as described above in Example 1 was performed with antimicrobial compositions that had been prepared on the basis of the recipes shown in Table 5.

TABLE 5

| Ingredients | Product 3 (wt. %) | Product D (wt. %) |
|---|---|---|
| Ethanol | 62 | 62 |
| Isopropyl alcohol | 3 | 3 |
| Niacinamide | 1 | 1 |
| Propylene glycol | 5 | 5 |
| Carbomer ® 980 | 0.350 | — |
| AMP-95 ® | 0.13 | — |
| Water | Up to 100% | Up to 100% |

Results

The results are displayed in the Table 6 below.

TABLE 6

|  | Viscosity (cps) | Residual log survival |
|---|---|---|
| Product 3 | 12000 | 2.13 |
| Product D | 0 | 3.18 |

The invention claimed is:

1. An antimicrobial composition for application onto human skin, said composition comprising:
   a. 55 to 70 wt. % ethanol and isopropanol;
   b. 0.75 to 1 wt. % niacinamide;
   c. 3 to 10 wt. % propylene glycol;
   d. 25 to 40 wt. % of water; and
   wherein the weight ratio of niacinamide to the propylene glycol is in the range of 1:2 to 1:20 and wherein the viscosity of the composition is in the range of 0.5 Pa s (500 cps) to 18 Pa s (18000 cps) at 25° C.;
   wherein the composition further comprises 0.05 to 0.8 wt. % of a thickening agent comprising polyacrylic acid; and
   0.1 to 0.13 wt. % of a basic neutralizer, wherein the neutralizer comprises aminomethylpropanol.

2. Antimicrobial composition according to claim 1, wherein the weight ratio of the niacinamide to the one or more polyols is in the range of 1:3 to 1:15.

3. Antimicrobial composition according to claim 1, wherein the composition comprises 0.75 wt. % of niacinamide.

4. Antimicrobial composition according to claim 1, wherein the composition is liquid at 20° C.

5. Antimicrobial composition according to claim 1, wherein the composition is monophasic.

6. Antimicrobial composition according to claim 1, wherein the viscosity of the composition is in the range of 1 Pa s (1000 cps) to 15 Pa s (15000 cps) at 25° C.

7. Antimicrobial composition according to claim 1, wherein the composition further comprises skin conditioning agents selected from silicones, siloxanes and combinations thereof.

8. A method of using the antimicrobial composition according to claim 1 as an antiseptic, comprising applying the antimicrobial composition onto the human skin.

9. Antimicrobial composition according to claim 1, comprising 25 to 30 wt. % water.

10. Antimicrobial composition according to claim 1, wherein the residual log survival is less than 3.

* * * * *